United States Patent
Dunn et al.

(10) Patent No.: US 6,225,062 B1
(45) Date of Patent: May 1, 2001

(54) METHOD AND KIT FOR DIRECT ISOTHERMAL SEQUENCING OF NUCLEIC ACIDS

(75) Inventors: James M. Dunn, Scarborough; Thomas J. Digby, Vancouver, both of (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 09/269,117

(22) PCT Filed: Nov. 12, 1997

(86) PCT No.: PCT/CA97/00848

§ 371 Date: Aug. 17, 1999

§ 102(e) Date: Aug. 17, 1999

(87) PCT Pub. No.: WO98/21361

PCT Pub. Date: May 22, 1998

Related U.S. Application Data

(60) Provisional application No. 60/031,257, filed on Nov. 12, 1996.

(51) Int. Cl.[7] .......................... C12P 19/34; C07H 21/02; C07H 21/04; C07H 21/00; C12N 15/00

(52) U.S. Cl. ........................... 435/6; 435/91.2; 435/91.1; 536/23.1; 536/24.33; 536/25.32; 536/25.3; 536/26.6; 935/77

(58) Field of Search ................................. 435/91.1, 91.2; 935/77; 536/23.1, 24.33, 25.32, 25.3, 26.6

(56) References Cited

U.S. PATENT DOCUMENTS 5,830,657 * 11/1998 Leushner et al. .................... 435/6

FOREIGN PATENT DOCUMENTS

WO 89/01749   3/1989 (WO).

(List continued on next page.)

OTHER PUBLICATIONS

Axelrod, V.D., et al, "Transcription from BacteriophageT7 and SP6 RNA Polymerase Promoters in the Presence of 3'-Deoxyribonucleoside 5'-Tripfosphate Chain Terminatoes", Biochemistry, vol. 24:5716–5723, 1985.

(List continued on next page.)

*Primary Examiner*—W. Gary Jones
*Assistant Examiner*—Joyce Tung
(74) *Attorney, Agent, or Firm*—Oppedahl & Larson LLP

(57) ABSTRACT

Direct determination of the sequence of an RNA sample is performed under isothermal conditions. An RNA sample containing a target nucleic acid is combined in a single reaction vessel with a reaction mixture containing two polynucleotide primers, a first primer that specifically hybridizes with a target sequence near the 3' end of the target nucleic acid, and a second primer that specifically hybridizes to the 3' end of an antisense copy of the target nucleic acid. At least one of the primers is labeled with a detectable label, and at least one of the first or second primer has an RNA polymerase transcription initiation signal at its 5' end, which signal does not specifically hybridize to the RNA target. The reaction mixture also contains ribonucleotide triphosphates for RNA synthesis, deoxyribonucleotide triphosphates for DNA synthesis, at least one type of dideoxynucleotide triphosphate chain-terminator, and enzymes with the activity of reverse transcriptase, RNAse H, RNA Polymerase and a low discrimination DNA Polymerase such as Thermo Sequenase™. The combined reactants are incubated under isothermal conditions for a length of time sufficient to generate chain-terminated reaction products, and the chain-termninated reaction products are then detected after electrophoretic separation.

16 Claims, 3 Drawing Sheets

FOREIGN PATENT DOCUMENTS

WO 96/02668    2/1996  (WO).
WO 96/14434    5/1996  (WO).

OTHER PUBLICATIONS

Klement, J.F., et al., "Sequencing of DNA Using T3 RNA Polymerase and Chain Terminating Ribonucleotide Analogs", Gene Anal Techn, vol. 3:59–66, 1986.

Parvin, J.D., et al., "Rapid RNA Sequencing Using Double-Stranded Template DNA, SP6 Polymerase, and 3'-Deoxynucleotide Triphosphates", DNA, vol. 5(2):167–171, 1986.

Sambrook et al. Molecular Cloning, second edition, pp. 8.11–8.17, 1989.*

* cited by examiner

SEQUENCE LISTING

<160> NUMBER OF SEQ ID NOS: 2

<210> SEQ ID NO: 1
<211> LENGTH: 29
<212> TYPE: DNA
<213> ORGANISM: Human immunodeficiency virus type 1
<220> FEATURE:
<223> OTHER INFORMATION: sequencing primer for gag gene

<400> SEQUENCE: 1
agtgggggga catcaagcag ccatgcaaa                                  29

<210> SEQ ID NO: 2
<211> LENGTH: 54
<212> TYPE: DNA
<213> ORGANISM: Human immunodeficiency virus type 1
<220> FEATURE:
<223> OTHER INFORMATION: sequencing primer for gag gene with RNA
      polymerase promoter

<400> SEQUENCE: 2
aattctaata cgactcacta tagggtgcta tgtcacttcc ccttggttct ctca      54

METHOD AND KIT FOR DIRECT ISOTHERMAL SEQUENCING OF NUCLEIC ACIDS

This is a national phase application under 35 U.S.C. 371 based on PCT/CA97/00848, which claims priority from US provisional application No. 60/031,257 filed Nov. 12, 1996.

BACKGROUND OF THE INVENTION

This invention is directed towards a method and kit for determining the nucleotide base sequence of a nucleic acid, particularly for use in routine clinical diagnostic procedures.

DNA sequence-based diagnosis has the potential to become a routine clinical diagnostic test, and is already available in several formats. See, for example, U.S. Pat. Nos. 5,545,527, 5,550,020 and 5,552,283 which are incorporated herein by reference. To fully realize the potential for DNA sequence-based diagnostics, however, the development of simplified, and preferably single-tube sequencing techniques will be important.

DNA sequencing technique are generally well known. Such sequencing is generally performed using techniques based on the "chain termination" method described by Sanger et al., *Proc. Nat'l Acad. Sci.* (USA) 74(12): 5463–5467 (1977). Basically, in this process, DNA to be tested is isolated, rendered single stranded, and placed into four vessels. In each vessel are the necessary components to replicate the DNA strand, i.e., a template-dependant DNA polymerase, a short primer molecule complementary to a known region of the DNA to be sequenced, and individual nucleotide triphosphates in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate (ddA).

In each vessel, each piece of the isolated DNA is hybridized with a primer. The primers are then extended, one base at a time to form a new nucleic acid polymer complementary to the isolated pieces of DNA. When a dideoxynucleotide is incorporated into the extending polymer, this terminates the polymer strand and prevents it from being further extended. Accordingly, in each vessel, a set of extended polymers of specific lengths are formed which are indicative of the positions of the nucleotide corresponding to the dideoxynucleic acid in that vessel. These sets of polymers are then evaluated using gel electrophoresis to determine the sequence.

Improvements to the original technique described by Sanger et al. have included improvements to the enzyme used to extend the primer chain. For example, Tabor et al. have described enzymes such as T7 DNA polymerase which have increased processivity, and increased levels of incorporation of dideoxynucleotides. (See U.S. Pat. No. 4,795,699 and EP-A1-0 655 506, which are incorporated herein by reference). More recently, Reeve et al. have described a thermostable enzyme preparation, called Thermo Sequenase™, with many of the properties of T7 DNA polymerase. *Nature* 376: 796–797 (1995). The literature supplied with the Thermo Sequenase™ product suggests dividing a DNA sample containing 0.5–2 mg of single stranded DNA (or 0.5 to 5 mg of double stranded DNA) into four aliquots, and combining each aliquot with the Thermo Sequenase™ enzyme preparation, one dideoxynucleotide termination mixture containing one ddNTP and all four dNTP's; and a dye-labeled primer which will hybridize to the DNA to be sequenced. The mixture is placed in a thermocycler and run for 20–30 cycles of annealing, extension and denaturation to produce measurable amounts of dye-labeled extension products of varying lengths which are then evaluated by gel electrophoresis.

DNA sequencing can be performed using these procedures on genomic DNA or cDNA (a DNA copy of mRNA). Alternatively, the direct sequencing of mRNA is known using techniques similar to DNA sequencing.

When low levels of substrate template are present, it is generally necessary to amplify its amount before sequencing reactions can be reliably performed. A well known method of amplifying a DNA strand is by the polymerase chain reaction ("PCR"). PCR methods are disclosed in U.S. Pat. Nos. 4,683,194, 4,683,195 and 4,683,202, which are incorporated herein by reference. RNA amplification may be effectively performed using techniques disclosed in U.S. Pat. Nos. 5,130,238, 5,409,818, 5,554,517 (See also Sooknanan, R., van Gemen, B., and Malek, L. T. "Nucleic Acid Sequence Based Amplification" in *Molecular Methods for Virus Detection* chp. 12 (Academic Press; 1995)), also incorporated herein by reference. A related RNA amplification method is disclosed by Gen-Probe patents WO 9101384, WO 9525180, WO 9503430, U.S. Pat. No. 5,399,491, incorporated herein by reference.

The instant invention discloses a simplified method of determining the sequence of a nucleic acid in a patient sample, in a one-pot or single tube sequencing reaction that does not rely on the PCR method.

It is an object of the invention to provide a method and kit for determining the nucleic acid sequence of an RNA molecule in an RNA sample obtained from a patient sample.

SUMMARY OF THE INVENTION

The method of the invention permits determination of the sequence of nucleotides in a target nucleic acid molecule under isothermal conditions. In accordance with the invention, an RNA sample containing a target nucleic acid is combined in a single reaction vessel with a reaction mixture containing first and second polynucleotide primers, wherein the first primer specifically hybridizes with a target sequence near the 3' end of the target nucleic acid, and the second primer specifically hybridizes to the 3' end of an antisense copy of the target nucleic acid, and wherein at least the first or second primer has a detectable label, and wherein at least one of the first or second primer has an RNA polymerase transcription initiation signal at its 5' end which signal does not specifically hybridize to the RNA target, ribonucleosides ATP, GTP, CTP and UTP or their analogues for RNA synthesis, deoxyribonucleosides dATP, dGTP, dCTP and dTTP or their analogues for DNA synthesis, at least one type of dideoxynucleoside chain terminating nucleoside, or its analogue, and enzymes with the activity of reverse transcriptase, RNAse H, RNA Polymerase and ThermoSequenase. The combined reactants are incubated under isothermal conditions for a length of time sufficient to generate chain-terminated reaction products, and the chain terminated reaction products are then detected after electrophoretic separation.

DETAILED DESCRIPTION OF THE INVENTION

Figure 1:
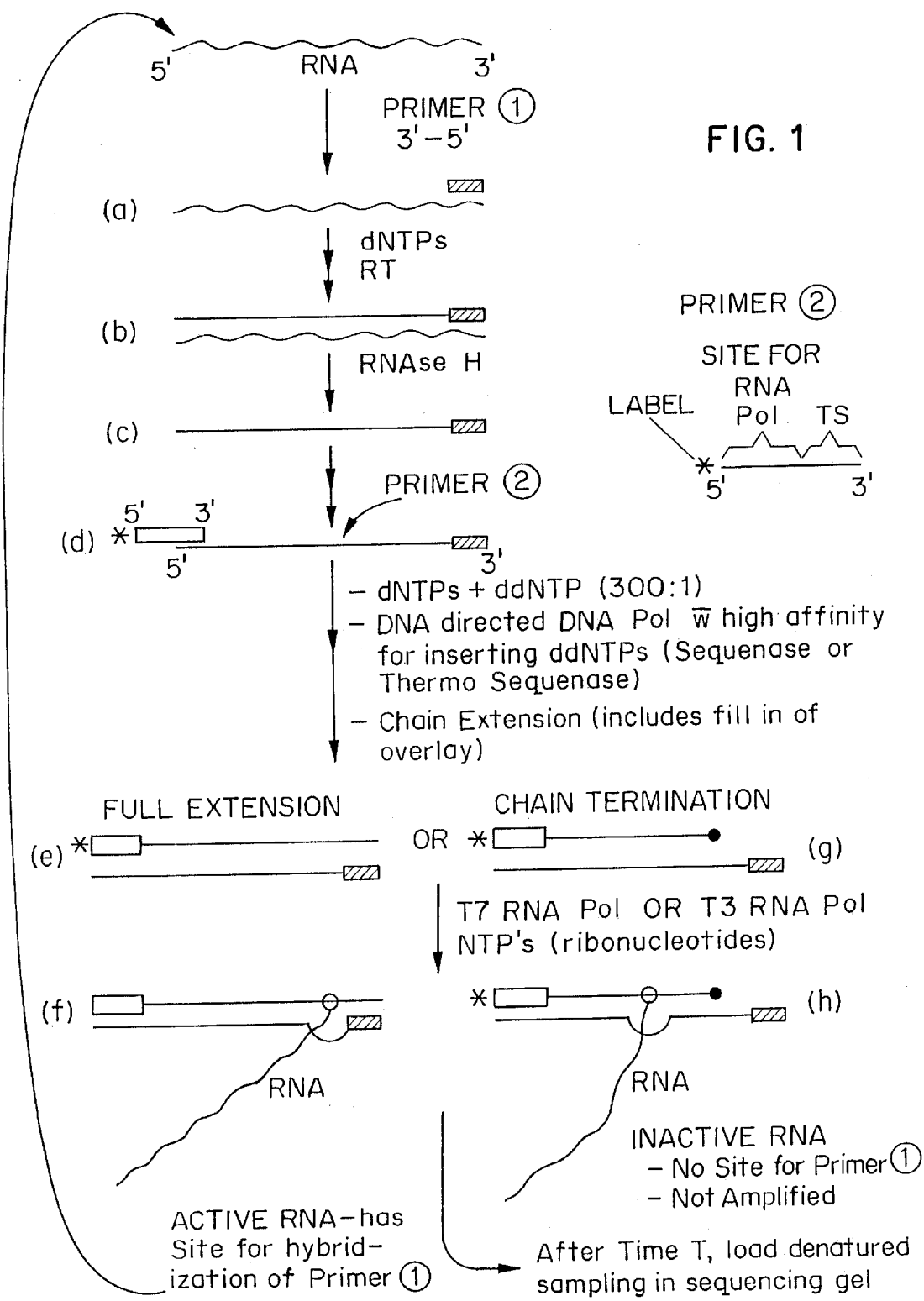
FIG. 1 shows a first embodiment of the method of the invention schematically.

The present invention provides a method for determining the nucleic acid sequence of an RNA molecule in an RNA sample obtained from a patient sample. The RNA molecule may be human or from an animal (particularly mammalian or avian) or may be from a pathogen such as a virus or bacteria which has contaminated the human or animal sample. Suitable patient samples include any tissue, blood, other organs, hair follicles, tumor samples extracted by biopsy or otherwise, or an excretion containing cells such as urine or sputum.

The RNA sample is prepared according to known methods, such as the preferred method for the NASBA reaction disclosed in Sooknanan et al., i.e., by silica pelleting. Care must be taken to prevent the contamination of the sample by the operator or by aerosol contaminants.

In a first embodiment of the invention, the nucleic acid sequence of the RNA molecule (the "target molecule") in the prepared RNA sample is determined by adding the RNA sample to a reaction mixture containing the following components:

(a) First Primer: a polynucleotide primer of 5–50 nt length which is capable of specific hybridization with a target sequence near the 3' end of the target molecule. This primer may be optionally labeled with a first detectable label, such as a fluorescent (e.g. Cy 5.5, FITC etc.) or radioactive moiety. This primer may also optionally have an RNA Polymerase promoter sequence at its 5' end, which sequence does not hybridize specifically with the target molecule.

(b) Second Primer: a polynucleotide primer of 5–50 nt length which is capable of specific hybridization with an anti-sense copy of the target sequence, near the 3' end of the anti-sense molecule. This primer may be optionally labeled with a second detectable label, different from the first detectable label of the first primer, such as a fluorescent or radioactive moiety. This primer may also optionally have an RNA Polymerase promoter sequence at its 5' end, which sequence does not hybridize specifically with the anti-sense copy of the target molecule.

(c) Reverse Transcriptase: a molecule, such as avian myeloblastosis virus (AMV) reverse transcriptase (Seikagaku, Rockville, Md.), with at least an RNA directed DNA Polymerase activity. This enzyme generates a cDNA copy of an RNA molecule.

(d) RNAse H: an enzyme which selectively degrades RNA in a DNA/RNA hybrid molecule. This activity may be included in the reverse transcriptase enzyme.

(e) Low Discrimination DNA Polymerase: a DNA directed DNA polymerase with a reduced ability to distinguish between dideoxyribonucleotides (ddNTPs) and deoxyribonucleotides (dNTPs), thus tending to incorporate chain-terminating ddNTPs in primer extension reactions. Preferred enzymes incorporate dideoxynucleotides into an extending nucleic acid polymer at a rate which is no less than about 0.4 times the rate of incorporation of deoxynucleotides. Examples of specific enzymes include ThermoSequenase(TM) (or related enzymes such as Sequenase 2.0) (Amersham Life Sciences, Cleveland, Ohio). This enzyme need not necessarily be heat stable since it is being used in an isothermal reaction.

(f) RNA Polymerase: an RNA polymerase such as T7 RNA Pol or T3 RNA Pol which recognizes the RNA Pol promoter sequence of the first or second primer.

(g) Ribonucleotide triphosphates (NTPs) and deoxyribonucleotide triphosphates (dNTPs): for nucleotide chain polymer synthesis (4 of each representing nucleotide bases A, C, G and T (or U for RNA)).

(h) At least one chain-terminating dideoxynucleotide triphosphate (ddNTP) for termination of chain extension at a selected base.

The above components are mixed in an appropriate buffer, in appropriate concentrations, to constitute the reaction mixture.

When the RNA sample is mixed with the reaction mixture and incubated, chain-terminated reaction products are formed which can be analyzed to determine the sequence of the initial sample. While not intending to be bound by any particular mechanism, these products are believed to be formed in the steps shown in FIG. 1.

First, as shown in step (a), the first primer hybridizes with the 3' end of the target molecule. Non-specific hybridization is minimized by selection of a suitably high temperature for the reaction (35–65 degrees C.). In step (b), primer extension begins with reverse transcriptase using dNTP monomers. Once the chain is extended, (c) the RNAse H activity will selectively degrade the original target molecule, leaving a single anti-sense DNA strand. (d) The second primer now hybridizes with the 3' end of the anti-sense DNA strand. Primer extension begins (e) with the DNA directed DNA polymerase, such as ThermoSequenase, and dNTP monomers are incorporated into the extending chain. Simultaneously, if the second primer has the non-hybridizing RNA promoter sequence, a "fill in" chain extension will add additional nucleotides onto the anti-sense DNA.

Because of the presence of the at least one ddNTP, two reaction products may result from the ThermoSequenase reaction. (f) If no ddNTP is incorporated in the nucleotide chain, a full length cDNA may be generated. This reaction product can serve as a template for synthesis of the target molecule by RNA Pol using NTP monomers, given that the second primer has an RNA Pol promoter sequence. Newly synthesized RNA can then join the reaction sequence at step (a). RNA Pol will produce very large numbers of RNA transcripts under isothermal conditions from a single cDNA (5 to 1000 copies), thus substantially amplifying the amount of target sequence.

The second reaction product (g) is the periodic chain termination product that results from incorporation of a ddNTP. Because the second primer has a detectable label on it, when the reaction products are separated by electrophoresis or otherwise (mass spectrometry, etc.), they can be detected and used for determining nucleotide sequence, in the Sanger et al. method.

It should be noted that even though a chain terminated product has an RNA Pol promoter on it (h), an RNA generated from it will not contain the first primer hybridization site, and will not, therefore, be amplified at the cDNA level.

From this discussion, it is evident that the proper dNTP-:ddNTP ratio needs to be ascertained, to generate a suitable amount of full length vs. chain terminated fragments. In the method of the invention, this ratio is determined to fall within the range 1:300 to 5000:1, preferably about 1000:1. The ratio of dNTP to ddNTP is the same for each type of nucleotide, A, C, G or T.

Figure 2:
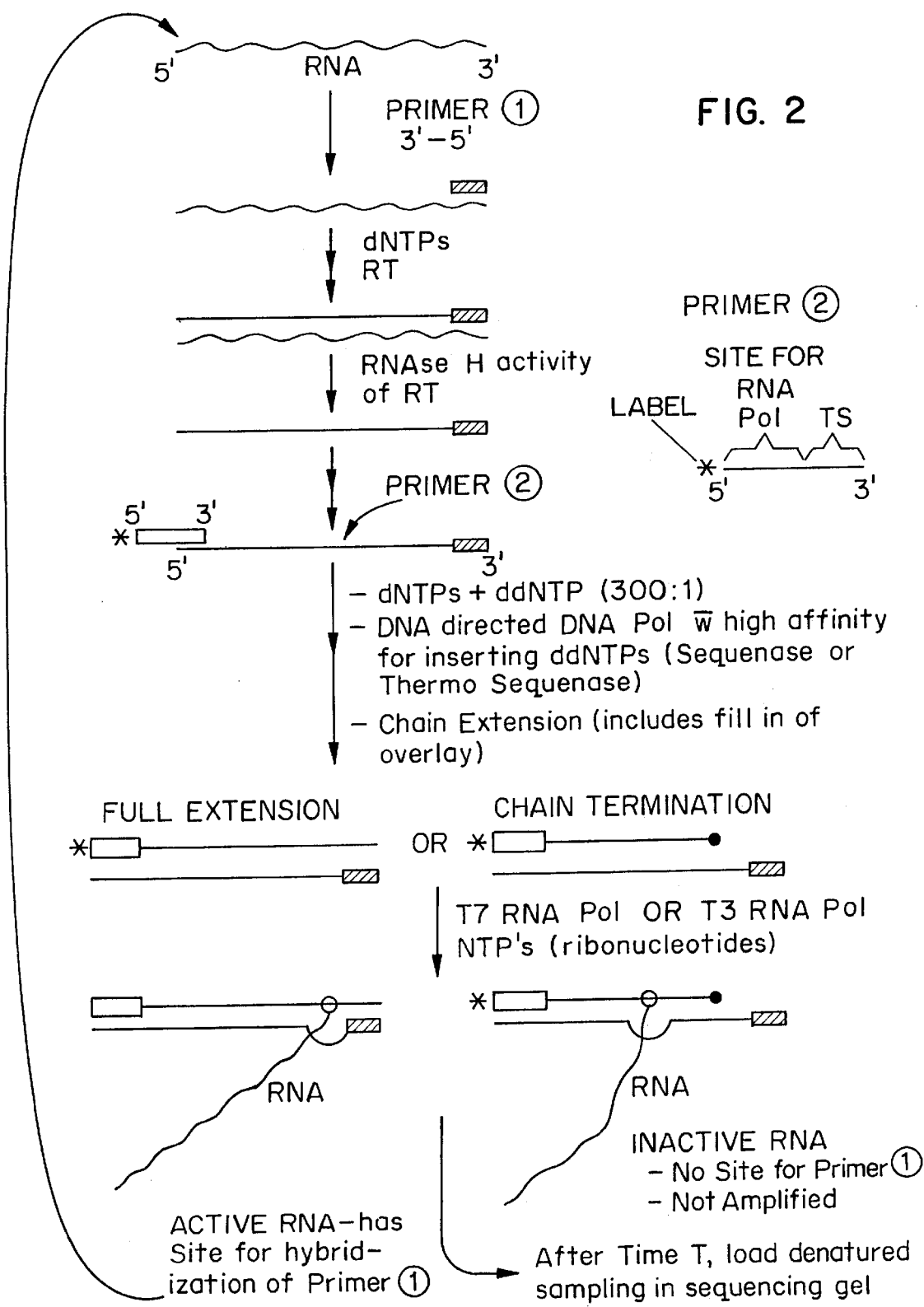
FIG. 2 shows a second embodiment of the method of the invention schematically.

The invention illustrated in FIG. 1 may be further improved by several additional enhancements. One such enhancement is illustrated in FIG. 2. This method relies on the observation that certain reverse transcriptase ("RT") enzymes such as Moloney Murine Leukemia Virus (MMLV) RT and MMLV RT have an inherent RNAse H activity (c.f. patent no. EP 408295). This permits the reaction to proceed from step (b) to step (c) in the absence of RNAse H itself, as long as the RT has this RNAse H activity.

Figure 3:
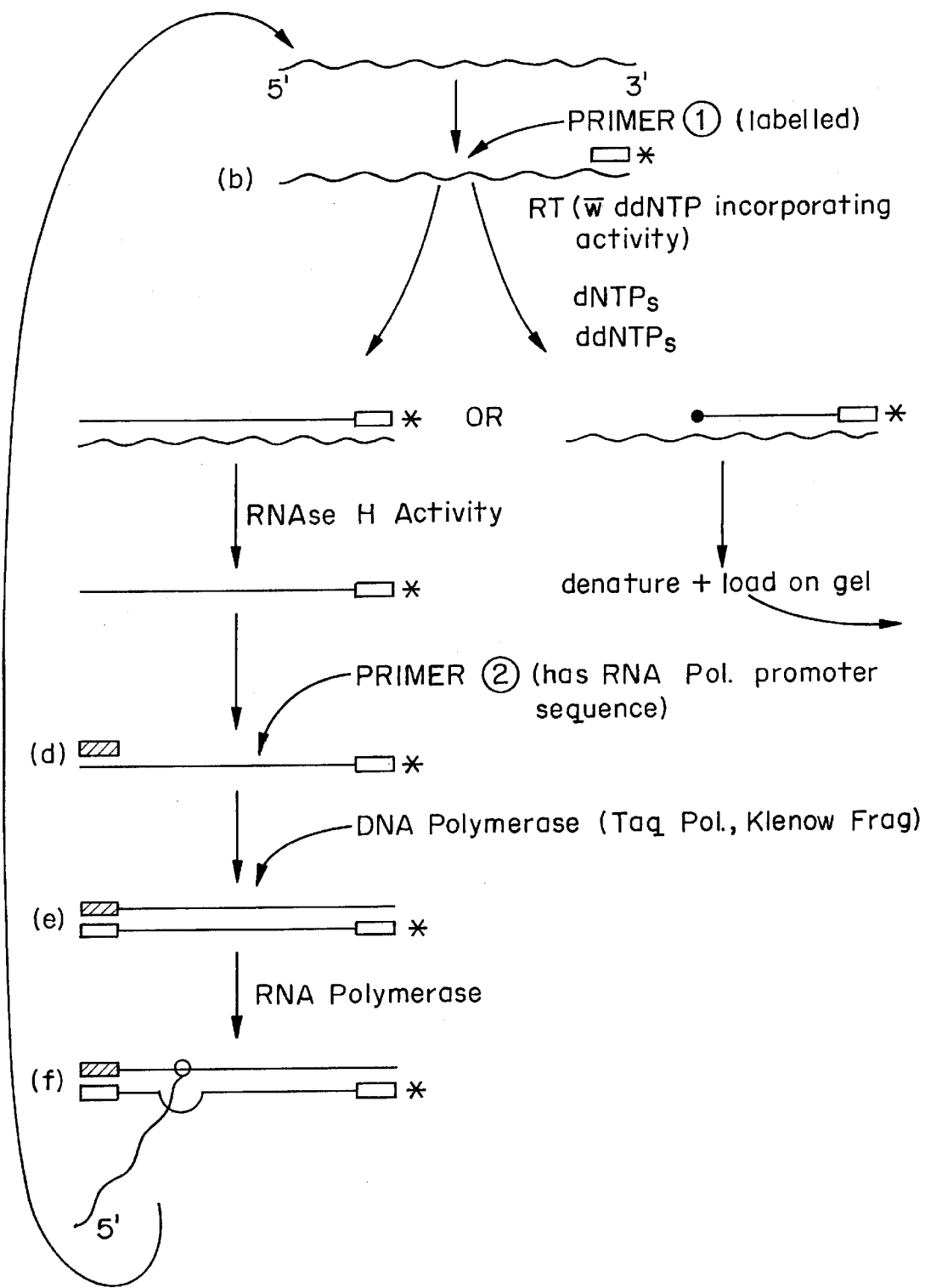
FIG. 3 shows a third embodiment of the method of the invention schematically.

Another enhancement, illustrated in FIG. 3 employs the finding, disclosed in EP 655506, that the ability of a DNA polymerase to distinguish between ddNTPs and dNTPs is influenced by a limited number of amino acids in the active site (ddNTP binding site) of the enzyme. This suggests that a reverse transcriptase could be engineered which has a reduced ability to distinguish between ddNTPs and dNTPs.

Wild type reverse transcriptase incorporates ddNTPs into a chain extending nucleotide rather poorly. For this reason, negligible amounts of ddNTPs are incorporated into the RT reaction (step (b) of FIG. 1), especially if the dNTP:ddNTP ratio is at the preferred concentration of 1000:1.

In fact, wild type reverse transcriptase will incorporate ddNTPs into a chain extending strand at a rate of 1 per 10 to 50 dNTPs, which is somewhat greater than wild type Taq Polymerase, *E. coli* DNA Pol I or T4 DNA Pol, where the incorporation rate is less than 1 per 1000. (See Sooknanan, page 284; or EP 655506). Remarkably, it is found that dideoxy resistant mutant DNA polymerases can be generated by modifying the single amino acid that corresponds to position 526 of T7 DNA Pol, position 762 of *E. coli* Pol 1 and 667 of Taq DNA polymerase. Such changes can provide a 250–8000 fold reduction in discrimination levels. Further, modification of at least 13 other sites in the molecule can reduce discrimination although the effect of these alterations is much less, only 5–20 fold.

Dideoxy resistant reverse transcriptase can be generated by site specific mutagenesis techniques. These techniques are well known in the art, (see Sarkar and Sommer 8 Biotechniques 404, 1990) and are explained in detail as they relate to DNA polymerases in EP 655506. Briefly, the technique involves the cloning and expression of mutant forms of a gene encoding a wild type enzyme. Mutations may be introduced either randomly or by site specific techniques. Expressed mutants are then assayed for ddNTP incorporation rates. Presumably, mutations corresponding to the dideoxyresistance mutations observed in other enzymes will be sufficient to create a dideoxy resistant reverse transcriptase. A series of experiments can be performed by anyone skilled in the art which would be reasonably expected to generate a dideoxy-resistant mutant of reverse transcriptase.

With such a non-discriminating RT, the method of the invention can be advanced. In FIG. 3 the RT chain extension at step (b) is the source of both the chain terminated fragments and full length fragments. The DNA directed DNA polymerase employed at step (d) is a high fidelity DNA polymerase, which is highly selective against ddNTP incorporation, such as *E. coli* DNA Pol I or Taq Polymerase. In this case, the first primer has the detectable label. The RT step (b) generates chain terminated fragments. Any fragments which are fully extended and not chain terminated are used to generate the second strand of the cDNA (d,e). The RNA template generated in step (f) feeds back into the cycle and can serve as the template for chain termination reactions. This method has the advantage that the RNA is the sequencing template, and it does not need to be converted into cDNA for chain termination reactions. Lower amounts of dNTPs can be usefully employed.

Practice of the method of the present invention can be facilitated by packaging the various enzymes and reagents used in the invention in kit form. For any given target molecule, such a kit includes:

(a) First Primer: a polynucleotide primer of 5–50 nt length which is capable of specific hybridization with a target sequence near the 3' end of the target molecule. This primer may be optionally labeled with a first detectable label, such as a fluorescent (e.g. Cy 5.5, FITC etc.) or radioactive moiety. This primer may also optionally have an RNA Polymerase promoter sequence at its 5' end, which sequence does not hybridize specifically with the target molecule.

(b) Second Primer: a polynucleotide primer of 5–50 nt length which is capable of specific hybridization with an anti-sense copy of the target sequence, near the 3' end of the anti-sense molecule. This primer may be optionally labeled with a second detectable label, different from the first detectable label of the first primer, such as a fluorescent or radioactive moiety. This primer may also optionally have an RNA Polymerase promoter sequence at its 5' end, which sequence does not hybridize specifically with the anti-sense copy of the target molecule.

(c) Enzymes providing reverse transcriptase activity, RNAse H activity, RNA Polymerase activity and DNA polymerase activity having reduced discrimination between dNTP and ddNTP substrates. The enzymes may be provided in individual packages or as a premixed composition containing all of the enzymes activities.

The kit may further contain Ribonucleosides (NTPs) and deoxyribonucleosides (dNTPs), one or more chain-terminating dideoxynucleoside (ddNTP) for termination of chain extension at a selected base, and appropriate buffers.

The following examples explain how to perform the method of the invention and to achieve its intended results. These examples are not intended to limit the scope of the invention in any way.

EXAMPLE 1

Preparation of RNA Sample

An RNA sample containing virus HIV-1 is prepared by adding 0.5–1.0 ml sample (serum of plasma) to a 15-ml conical screw cap tube containing 9.0 ml lysis buffer (120 g GuSCN, 2.6 g Triton X-100, 100 ml L2 buffer (12.1 g/l Tris-HCl pH6.4), 22 ml 0.2M EDTA, pH 8.0, final volume 222 ml). Invert tubes to mix. Add 70 ul silica suspension and vortex tube for 5 sec. Leave to 10 1 min at room temp (18–25 deg. C.). Invert every minute to mix. Centrifuge at 1500 g for 2 min. Remove supernatant using a 10 ml plastic pipette, leaving about 0.5 ml residual fluid. Remove residual fluid with sterile pipette without disturbing the pellet. Add 1 ml wash buffer (120 GuSCN, 100 ml L2 buffer) and resuspend silica by vortexing. Transfer silica suspension to a 1.5 ml microfuge tube. Centrifuge at 10,000 g for 15 sec. Remove supernatant with sterile pipette. Wash the silica pellet four times, one with wash buffer, twice with 70% ethanol and once with acetone.

Dry silica pellet completely by placing the opened tube in a heating block at 56 deg. C. for 10 1 min. Cover the tube with tissue to avoid aerosol contamination. Add 100 ul elution buffer (0.211 g Tris-HCl, pH 8.5/l, sterile) or water and resuspend pellet by vortexing. Incubate at 56 deg. C. for 10 1 min to elute the nucleic acid. Centrifuge at 10,000 g for 2 min. Transfer supernatant to a new microfuge tube without disturbing the pellet. Store at −70 deg. C.

EXAMPLE 2

Direct Isothermal Sequencing

From stock solutions prepare the following reaction mixture in a nuclease free microfuge tube.

| Component | Concentration | Volume |
|---|---|---|
| buffer | 2.5 X | 10 ul |
| Dithiothreitol | 250 mM | 1 ul |
| Primer mixture | 4 X | 6.25 ul |
| Nuclease-free Water | | to 18 ul | buffer 2.5×: 100 mM Tris, pH 8.5, 125 mM KCl, 30 mM MgCl2, 2.5 mM each dNTP (dATP, dGTP, dCTP, dTTP), 5 mM each NTP (ATP, GTP, CTP, UTP), 10 uM one or more chain terminating dideoxynucleoside (ddATP, ddCTP, ddGTP, ddTTP)
Primer Mixture: 5 pmol first primer, 5 pmol second primer, 3.75 ul 100% DMSO, Water (nuclease free) to 6.25 ul.
First Primer 5'-AGTGGGGGGACATCAAGCAGC CATGCAAA-3' SEQ ID No. 1
Second Primer 5'-AATTCTAATACGACTCACTATAGGG -TGCTATGTCACTTCCCCTTGGTTCTCTCA-3' SEQ ID No. 2
These sequences to gag gene mRNA of HIV-1. The second primer is chimeric, the first section being a T7 RNA Polymerase promoter.

The second primer is labeled on its 5' end. The label selected depends on the detection apparatus to be employed. For use with a MicroGene BlasterÔ (Visible Genetics Inc, Toronto, Canada) a suitable label is the fluorescent dye Cy5.5 (Amersham Life Sciences, Cleveland, Ohio) conjugated to the 5' terminal nucleotide of the primer, by a dye-ester linkage.

Vortex the reaction mixture briefly and aliquot 18 ul into a nuclease free 1.5 ml microfuge tube. Add 5 ul RNA sample and mix by tapping. Incubate at 65 deg. C for 5 min. Transfer to a 40 1 deg. C. water bath, and equilibrate for 5 mins.

Add 2 ul Enzyme Mixture* to the reaction tubes and gently mix by tapping. Centrifuge at 10,000 g for 5 sec. Incubate at 40 1 deg. C. for 90 mins. Centrifuge briefly to collect condensate. Place on ice until ready for loading.

* Enzyme Mixture—0.13 ul 20 mg/ml BSA (in 50% glycerol; Boehringer Mannheim), 8 U AMV reverse transcriptase (Seikagaku), 0.2 U *E. coli* RNase H (Pharmacia), 40 U T7 RNA Polymerase (Pharmacia) and 3 U ThermoSequenase (Amersham Life Sciences, Cleveland, Ohio).

When ready for loading and observing detectable reaction products, the reaction products are mixed with an equal volume of STOP/Loading buffer (Formamide, colored dye) and mixed well. 1.5 ul of the resulting mix is loaded per lane of a MicroCel™ gel electrophoresis cassette loaded in a MicroGene Blaster™ DNA sequencer. The sample is electrophoresed and detected by the automated laser detection system. Results are stored in a computer and analyzed by GeneObjects™ Software (Visible Genetics Inc., Toronto, Canada).

What is claimed is:

1. A method of determining the sequence of nucleotides in a target ribonucleic acid under isothermal conditions comprising the steps of:
   (a) combining in a single reaction vessel
       an RNA sample containing a target ribonucleic acid,
       first and second polynucleotide primers, wherein the first primer specifically hybridizes with a target sequence near the 3' end of the target ribonucleic acid, and the second primer specifically hybridizes to the 3' end of an antisense copy of the target ribonucleic acid, and wherein at least the first or second primer has a detectable label, and wherein at least one of the first or second primer has an RNA polymerase transcription initiation signal at its 5' end which signal does not specifically hybridize to the target ribonucleic acid,
       ribonucleotide triphosphates for RNA synthesis,
       deoxyribonucleotide triphosphates for DNA synthesis,
       at least one type of chain terminating nucleotide triphosphate,
       and enzymes with the activity of reverse transcriptase, RNase H, RNA Polymerase and a low discrimination DNA Polymerase having reduced discrimination between dNTP and ddNTP substrates;
   (b) incubating the combined reactants under isothermal conditions for a length of time sufficient to generate chain-termninated reaction products, and
   (c) detecting chain termninated reaction products after electrophoretic separation, said chain terminated reaction products reflecting the sequence of nucleotides in the target ribonucleic acid.

2. The method of claim 1, wherein the low discrimination DNA polymerase incorporates dideoxynucleotides into an extending nucleic acid polymer at a rate which is no less than about 0.4 times the rate of incorporation of deoxynucleocides.

3. The method according to claim 1, wherein at least one enzyme having both reverse transctiptase and RNase H activity is included in the reaction mixture.

4. The method according to claim 3, wherein the enzyme having both reverse transcriptase and RNase H activity is included in the reaction mixture is selected from among avian myeloblastosis virus (AMV) reverse transcriptase and Moloney murine leukemia virus (MMLV) reverse transcriptase.

5. The method according to claim 1, wherein the deoxynucleotide triphosphates and the chain terminating nucleotide triphosphate are present in a mole ratio of from 1:300 to 5000:1.

6. A kit for isothermal sequencing of a target RNA molecule comprising, in packaged combination,
   (a) a first polynucleotide primer of 5–50 nt length which is capable of specific hybridization with a target sequence near the 3' end of the target RNA molecule
   (b) a second polynucleotide primer of 5–50 nt length which is capable of specific hybridization with an anti-sense copy of the target RNA molecule; and
   (c) enzymes sufficient to provide reverse transcriptase activity, RNAse H activity, RNA Polymerase activity and low discrimination DNA polymerase activity having reduced discrimination between dNTP and ddNTP substrates, wherein at least one of the first and second primers is labeled with a detectable label and wherein at least one of the first and second primers includes an RNA polymerase initiation signal at the 5'-end thereof, which signal does not specifically hybridize with the target RNA molecule.

7. The kit according to claim 6, wherein the low discrimination DNA polymerase incorporates dideoxynucleotides into an extending nucleic acid polymer at a rate which is no less than about 0.4 times the rate of incorporation of deoxynucleotides.

8. The kit according to claim 6, wherein at least one enzyme having both reverse transcriptase and RNase H activity is included in the kit.

9. The kit according to claim 6, wherein at least one of the first or second primers is labeled with a fluorescent label.

10. The method of claim 2, wherein at least one enzyme having both reverse transcriptase and Rnase H activity is included in the reaction mixture.

11. The method of claim 2, wherein the deoxynucleotide triphosphates and the chain terminating nucleotide triphosphate are present in a mole ratio of from 1:300 to 5000:1.

12. The method of claim 3, wherein the deoxynucleotide triphosphates and the chain terminating nucleotide triphosphate are present in a mole ratio of from 1:300 to 5000:1.

13. The method of claim 4, wherein the deoxynucleotide triphosphates and the chain terminating nucleotide triphosphate are present in a mole ratio of from 1:300 to 5000:1.

14. The kit of claim 7, wherein at least one enzyme having both reverse transcriptase and RNase H activity is included in the kit.

15. The kit of claim 7, wherein at least one of the first or second primers is labeled with a fluorescent label.

16. The kit of claim 8, wherein at least one of the first or second primers is labeled with a fluorescent label.

* * * * *